Figure 1:
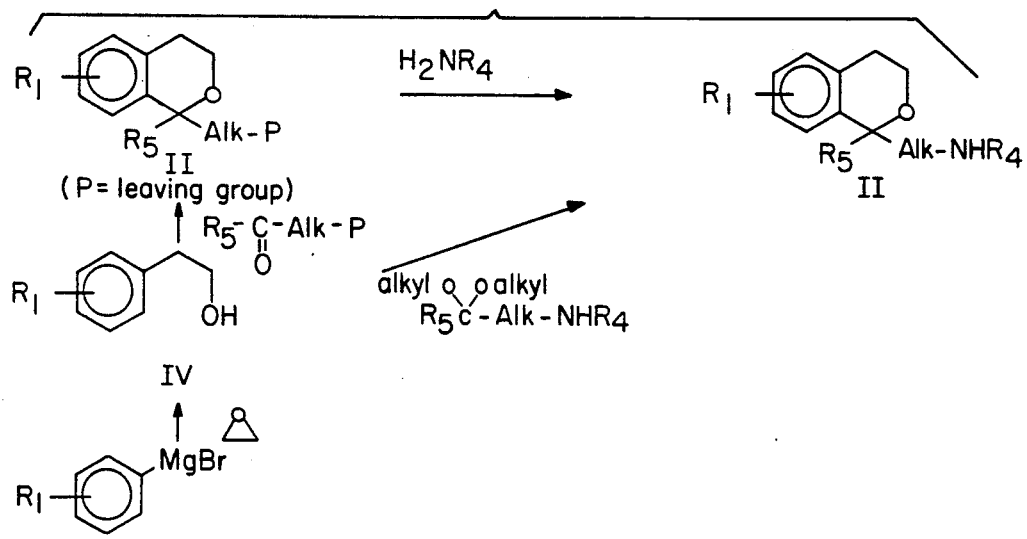

United States Patent [19]
Combourieu et al.

[11] Patent Number: 5,137,911
[45] Date of Patent: Aug. 11, 1992

[54] ISOCHROMANE DERIVATIVES

[75] Inventors: Michael Combourieu, Cebazat; Jean-Claude Laigle, Riom, both of France

[73] Assignee: Akzo N.V., Arnhem, Netherlands

[21] Appl. No.: 679,374

[22] Filed: Apr. 2, 1991

[30] Foreign Application Priority Data

Apr. 2, 1990 [EP] European Pat. Off. ........ 90400892.7

[51] Int. Cl.$^5$ ............... A61K 31/35; C07D 493/06
[52] U.S. Cl. .................. 514/452; 514/454; 514/456; 514/464; 549/387; 549/395; 549/398; 549/407; 549/408
[58] Field of Search ............... 549/387, 398, 407, 395, 549/408; 514/452, 454, 456, 464

[56] References Cited

U.S. PATENT DOCUMENTS 4,563,458  1/1986  Widdig et al. .................. 549/387
4,654,362  3/1987  Van Lommen et al. ........... 549/387

FOREIGN PATENT DOCUMENTS 0157206  10/1985  European Pat. Off. .
1552004  9/1979  United Kingdom .

Primary Examiner—C. Warren Ivy
Assistant Examiner—Ba K. Trinh
Attorney, Agent, or Firm—William M. Blackstone

[57] ABSTRACT

An isochromane derivative having the general formula I

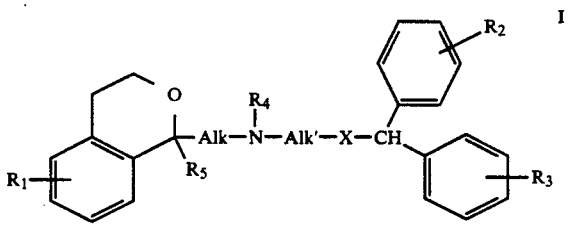

in which
each of $R_1$, $R_2$, and $R_3$ is one to four substituents independently selected from hydrogen, hydroxy, alkyl (1–4 C), alkoxy (1–4 C), halogen, or $CF_3$, or represents a methylenedioxy group;
$R_4$ is selected from hydrogen or alkyl (1–4 C);
Alk is an alkylene group with 1–4 carbon atoms;
Alk' is an alkylene group with 2–4 carbon atoms, when $R_5$ is selected from hydrogen or alkyl (1–4 C) and X is O or S; or
Alk' is an alkylene group with 1–4 carbon atoms or a bond, when $R_5$ is an alkyl (1–4 C) group and X is $CH_2$ or a bond;
or a pharmaceutically acceptable salt thereof.

4 Claims, 1 Drawing Sheet

ISOCHROMANE DERIVATIVES

The invention concerns isochromane derivatives with the general formula I

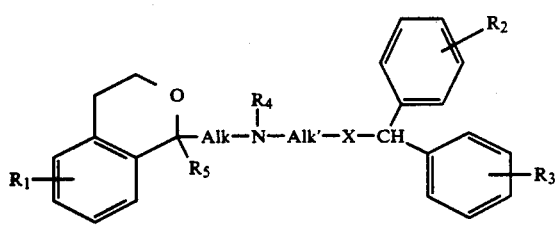

in which
each of $R_1$, $R_2$, and $R_3$ is one to four substituents independently selected from hydrogen, hydroxy, alkyl (1-4 C), alkoxy (1-4 C), halogen, or $CF_3$, or represents a methylenedioxy group;
$R_4$ is selected from hydrogen or alkyl (1-4 C);
Alk is an alkylene group with 1-4 carbon atoms;
Alk' is an alkylene group with 2-4 carbon atoms, when $R_5$ is selected from hydrogen or alkyl (1-4 C) and X is O or S; or
Alk' is an alkylene group with 1-4 carbon atoms or a bond, when $R_5$ is an alkyl (1-4 C) group and X is $CH_2$ or a bond;
or a pharmaceutically acceptable salt thereof.

The compounds of this invention are potent intracellular calcium antagonists, which inhibit contractile responses induced by $Ca^{++}$ channel activation as well as $Ca^{++}$ release processes triggered by a variety of agonists, and can be used in the treatment of angina pectoris, cardiac dysrhytmias, hypertension, and cardiomyopathies.

The compounds are also strong inhibitors of blood platelet aggregation, and therefore suitable drugs for the treatment of cerebral ischaemia, stroke, sudden death, and myocardial infarction.

The term halogen used in the definition of formula I means fluorine, chlorine, bromine or iodine. Fluorine is the preferred halogen.

The term alkyl (1-4 C) means a branched or unbranched alkyl group with 1-4 carbon atoms, such as methyl, ethyl, propyl, isopropyl, butyl, tert-butyl and the like.

The alkyl moiety which is present in the alkoxy (1-4 C) group has the same meaning as previously defined for alkyl (1-4 C).

The term Alk means a saturated branched or unbranched aliphatic alkylene group with 1-4 carbon atoms. Examples are 1,2-ethanediyl, 1,3-propanediyl, 1,4-butanediyl, and 1-methyl-1,2-ethanediyl. The preferred Alk groups are unbranched alkylene groups with 1-3 carbon atoms. Most preferred is the 1,2-ethanediyl group.

The term Alk' means a saturated branched or unbranched aliphatic alkylene group with 2-4 carbon atoms when X is O or S, or it means a saturated branched or unbranched aliphatic alkylene group with 1-4 carbon atoms or a bond when X is $CH_2$ or a bond. Examples are 1,2-ethanediyl, 1,3-propanediyl, 1,4-butanediyl, and 1-methyl-1,2-ethanediyl. The preferred Alk' group is 1,2-ethanediyl.

Preferred isochromane derivatives according to the invention have formula I, in which $R_1$ represents one or two methoxy groups, or in which $R_1$ represents two adjacent substituents being a methylenedioxy group, $R_2$ and $R_3$ are hydrogen or halogen, $R_4$ is hydrogen or alkyl (1-4 C), Alk is an unbranched alkylene group with 1-3 carbon atoms, Alk' is 1,2-ethanediyl, and X is O or S, and $R_5$ is selected from hydrogen or alkyl (1-4 C); or a pharmaceutically acceptable salt thereof.

The most preferred compound is the isochromane derivative having the formula

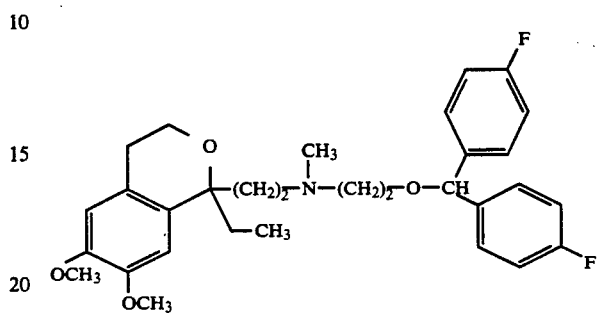

or a pharmaceutically acceptable salt thereof.

The novel compounds of formula I may be isolated from a reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, among which the racemic mixture. Methods for obtaining the pure enantiomers are well known in the art, e.g. synthesis with chiral induction or crystallization of salts which are obtained from optically active acids and the racemic mixture.

The compounds of the invention may be prepared by methods in use for analogous compounds. A suitable method, for instance, is the condensation of compound II with compound III,

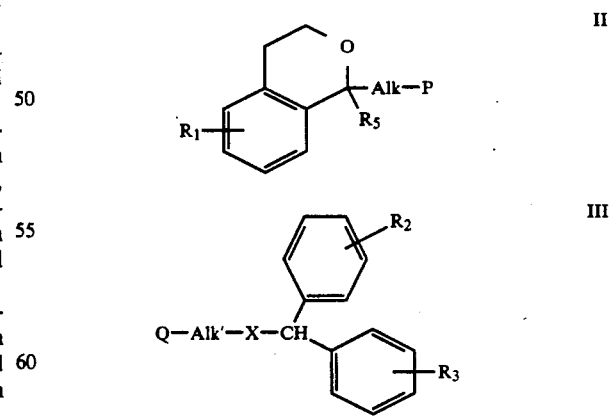

which $R_1$-$R_3$, $R_5$, X, Alk and Alk' have the previously given meanings, P is a leaving group and Q is the group $NHR_4$, or P is the group $NHR_4$ and Q is a leaving group, in which $R_4$ has the previously given meaning. The leaving group is a group commonly used as leaving group, such as a mesylate or tosylate group, or a halogen, such as chlorine or bromine.

An alternative method is the condensation of compound IV

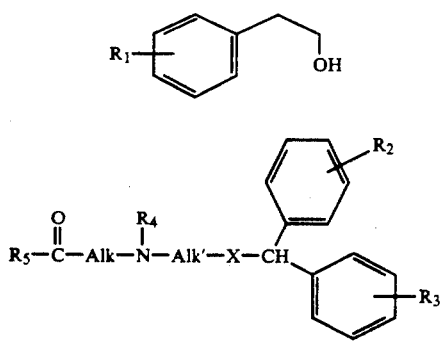

in which $R_1$–$R_5$, X, Alk and Alk' have the previously given meanings.

Figure 2:
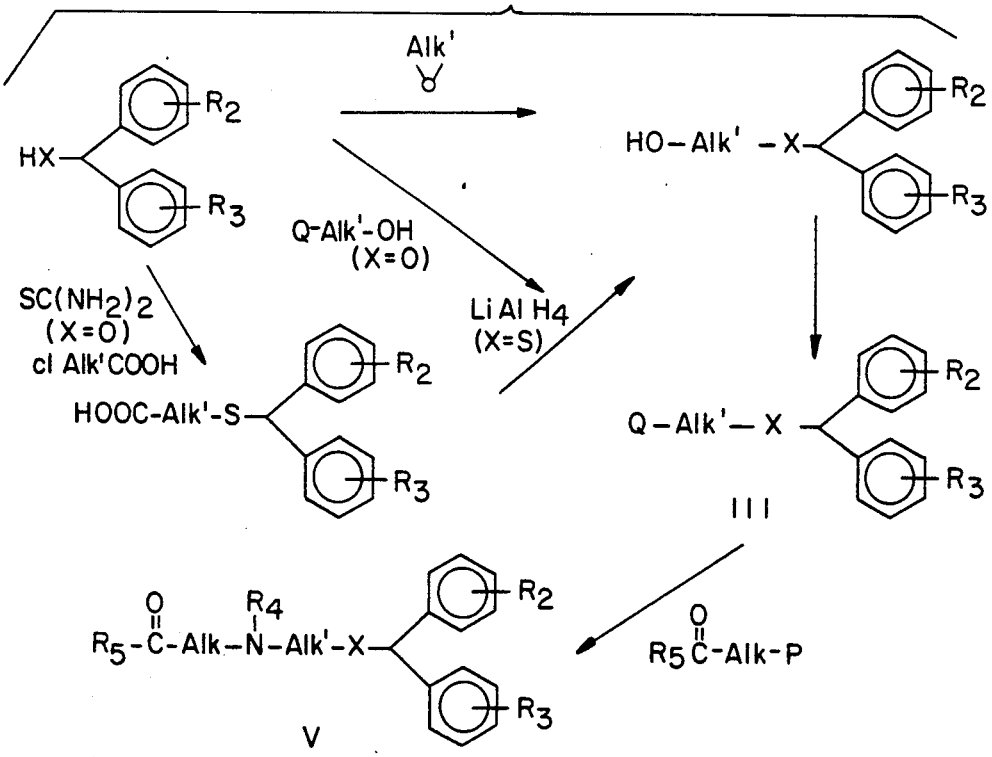

Starting products II–V are easily available according to methods generally known in organic chemistry. Some approaches for the preparation of compounds II–V are, as an example, depicted in FIGS. 1 and 2.

It is possible to convert the products obtained by one of the previously mentioned procedures into another product according to the invention. Using generally known methods it is, for instance, possible to convert aromatic substituents into other aromatic substituents. Alkoxy substituents may be treated with strong acids such as $BBr_3$, to give the hydroxy substituent. Hydroxy substituted compounds may be condensed with lower alcohols in acidic medium to give alkoxy derivatives, and ortho-dihydroxy substituted compounds may be condensed with formaldehyde to give methylenedioxy substituted derivatives. Compounds wherein $R_4$ is hydrogen may be alkylated, e.g. by a Leuckart-Wallach reaction, to afford compounds wherein $R_4$ is alkyl.

The compounds of the invention may be administered enterally or parenterally, and for humans preferably in a daily dosage of 0.01–50 mg per kg body weight. Mixed with pharmaceutically suitable auxiliaries, e.g. as described in the standard reference, Chase et al., Remington's Pharmaceutical Sciences, the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray.

The invention is further illustrated by the following examples.

EXAMPLE 1

1-ethyl-N-[2-[bis(4-fluorophenyl)methoxy]ethyl]-3,4-dihydro-6,7-dimethoxy-N-methyl-1H-2-benzopyran-1-ethanamine ($\pm$)-2,3-dihydroxybutanedioate (1:1) salt a. A mixture of 91.3 g of 3,4-dimethoxyphenethyl alcohol and 600 ml of a 33% solution of methylamine in absolute ethanol (8.03 mol/l) was brought into a sealed vessel and placed in an autoclave at 110°–130° C. for 2 h. The solvent was evaporated and the concentrate dissolved in a mixture of 500 ml of water and 500 ml of ethylacetate. The aqueous phase was basified and extracted into ethyl acetate. The organic layer was washed with water, dried over sodium sulphate and evaporated to give 70.1 g (78,2%) of 1-ethyl-3,4-dihydro-6,7-dimethoxy-N-methyl-1H-2-benzopyran-1-ethanamine.

b. To a solution of 29,3 g of 2-chloroethanol in toluene 2 ml of concentrated sulphuric acid were added, after which 50 g of 4,4'-difluorobenzhydrol were added under stirring. The mixture was refluxed for 2 h, cooled and more toluene added. The organic phase was washed successively with water, aqueous sodium carbonate, and water and then dried. The solvent was evaporated to give 65 g of a crude product which was distilled to obtain 57.5 g (89,5%) of [1-(2-chloroethyl)]-bis-(4-fluorophenyl)methane.

c. A mixture of 45 g of 1-ethyl-3,4-dihydro-6,7-dimethoxy-N-methyl-1H-2-benzopyran-1-ethanamine, 50 g of [1-(2-chloroethyl)]-bis-(4-fluorophenyl)methane, and 24.5 g of potassium carbonate in 500 ml of dimethylformamide was heated at 120°–140° C. for 2 h. The mixture was hydrolyzed with 1 l of water, extracted twice with 300 ml of diethylether and the organic phase was washed with water, dried and evaporated. The crude base was converted into the ($\pm$)-tartrate with ($\pm$)-tartaric acid in ethylacetate to give 60 g (55%) of 1-ethyl-N-[2-[bis(4-fluorophenyl)methoxy]ethyl]-3,4-dihydro-6,7-dimethoxyN-methyl-1H-2-benzopyran-1-ethanamine ($\pm$)-2,3-dihydroxybutanedioate (1:1) salt. m.p. 118.5° C.

EXAMPLE 2

In an analogous manner as described in Example 1 was prepared:
1-ethyl-3,4-dihydro-6,7-dimethoxy-N-methyl-N-[2-(diphenylmethoxy)ethyl]-1H-2-benzopyran-1-ethanamine ($\pm$)-2,3-dihydroxybutanedioate (1:1) salt. m.p. 99.3° C.
1-ethyl-N-[4-[bis(4-fluorophenyl)butyl]-3,4-dihydro-6,7-dimethoxy-N-methyl-1H-2-benzopyran-1-ethanamine ($\pm$)-2,3-dihydroxybutanedioate (1:1) salt. m.p. 75° C.

EXAMPLE 3

1-ethyl-N-[2-bis(4-fluorophenyl)methylthio]ethyl]-3,4-dihydro-6,7-dimethoxy-N-methyl-1H-2-benzopyran-1-ethanamine, a. 12.1 g of 4,4'-difluorobenzhydrol were added to a mixture of 5 g of thiourea, 30 ml of 48% hydrobromic acid, and 4.5 ml of water at 60° C., and then further heated at 95° C. for another hour. The mixture was cooled and the crystals were filtered off and washed with water. The crystals were mixed with 30 ml of water and 18 ml of 40% NaOH, and heated at 70° C. Then 5.7 g of chloroacetic acid and 11 ml of water were cautiously added and the mixture was refluxed for 30 min. After cooling the mixture was extracted into dichloromethane, washed, dried, and evaporated. After addition of pentane 11.9 g (73,1%) of bis(4-fluorophenyl)methylthioacetic acid solidified.

b. 11.5 g of bis(4-fluorophenyl)methylthioacetic acid dissolved in a minimum amount of diethylether were added to a suspension of 1.8 of lithium aluminum hydride in 500 ml of anhydrous ether. The mixture was refluxed for 2 h and after the usual work-up 10.5 g (96.3%) of crude 2-[bis(4-fluorophenyl)methylthio]ethanol were obtained.

c. A mixture of 10.5 g of 2-[bis(4-fluorophenyl)methylthio]ethanol, 5.3 g of thionyl chloride, and 50 ml of dichloromethane was evaporated to dryness. The residue was dissolved in dichloromethane, washed twice with water, dried and concentrated. After distillation 7.4 g (67.3%) of 1-chloro-2-[bis(4-fluorophenyl)methylthio]ethane were obtained.

d. In an analogous manner as described in Example 1c, 1-ethyl-N-[2-[bis(4-fluorophenyl)methylthio]ethyl]-3,4-dihydro-6,7-dimethoxy-N-methyl-1H-2-benzopyran-1-ethanamine was prepared from 1-chloro-2-[bis(4-fluorophenyl)methylthio]ethane and 1-ethyl-3,4-dihydro-6,7-dimethoxy-N-methyl-1H-2-benzopyran-1-ethanamine.

EXAMPLE 4

N-[2-[bis(4-fluorophenyl)methoxy]ethyl]-3,4-dihydro-6,7-dimethoxy-N-methyl-1H-2-benzopyran-1-ethanamine (±)-2,3-dihydroxybutanedioate (1:1) salt.

a. A mixture of 28.6 g of 3,4-dimethoxy-phenethyl alcohol and 26.2 g of 3-chloropropionaldehyde diethylacetal in 350 ml of absolute ethanol saturated with anhydrous hydrochloric acid was stirred for 24 h at ambient temperature. The solvent was evaporated and the residue distilled to give 34.2 g (83,4%) of 1-(2-chloroethyl)-3,4-dihydro-6,7-dimethoxy-N-methyl-1H-2-benzopyran.

b. In an analogous manner as described in Example 1a 3,4-dihydro-6,7-dimethoxy-N-methyl-1H-2-benzopyran-1-ethanamine was prepared.

c. In an analogous manner as described in Example 1c N-[2-[bis(4-fluorophenyl)methoxy]ethyl]-3,4-dihydro-6,7-dimethoxy-N-methyl-1H-2-benzopyran-1-ethanamine (±)-2,3-dihydroxybutanedioate (1:1) salt, m.p. 64° C., was prepared from 3,4-dihydro-6,7-dimethoxy-N-methyl-1H-2-benzopyran-1-ethanamine and 1-(2-chloroethyl)-3,4-dihydro-6,7-dimethoxy-N-methyl-1H-2-benzopyran.

EXAMPLE 5

In an analogous manner, as described in Example 4, were prepared:

N-[2-[bis(4-fluorophenyl)methoxy]ethyl]-3,4-dihydro-6,7-dimethoxy-N-methyl-1H-2-benzopyran-1-methanamine, (syrup).

N-butyl-1-ethyl-N-[2-[bis(4-fluorophenyl)methoxy]ethyl]-3,4-dihydro-6,7-dimethoxy-1H-2-benzopyran-1-ethanamine hydrochloride (1:1) salt, m.p. 158° C.

1-ethyl-N-[2-[bis(4-fluorophenyl)methoxy]ethyl]-3,4-dihydro-6,7-dimethoxy-N-(1-methylethyl)-1H-2-benzopyran-1-ethanamine, (syrup).

1-ethyl-N-[2-[bis(4-fluorophenyl)methoxy]ethyl]-3,4-dihydro-6,7-dimethoxy-1H-2-benzopyran-1-ethanamine, (syrup).

1-ethyl-N-[2-[bis(4-fluorophenyl)methoxy]ethyl]-3,4-dihydro-6,7-methylenedioxy-N-methyl-1H-2-benzopyran-1-ethanamine (±)-2,3-dihydroxybutanedioate (1:1) salt, m.p. 102,5 ° C.

1-ethyl-N-[2-[bis(4-fluorophenyl)methoxy]ethyl]-3,4-dihydro-6-methoxy-N-methyl-1H-2-benzopyran-1-ethanamine (E)-2-butenedioate (1:1) salt.

1-ethyl-N-[2-[bis(4-chlorophenyl)methoxy]ethyl]-3,4-dihydro-6,7-dimethoxy-N-methyl-1H-2-benzopyran-1-ethanamine (±)-2,3-dihydroxybutanedioate (1:1) salt, m.p. 135 ° C.

1-ethyl-N-[2-[bis(3-fluorophenyl)methoxy]ethyl]-3,4-dihydro-6,7-dimethoxy-N-methyl-1H-2-benzopyran-1-ethanamine, (syrup).

1-ethyl-3,4-dihydro-6,7-dimethoxy-N-[2-[bis(4-methoxyphenyl)methoxy]ethyl]-N-methyl-1H-2-benzopyran-1-ethanamine, (syrup).

N-[2-[bis(4-fluorophenyl)methoxy]ethyl]-3,4-dihydro-6,7-dimethoxy-1,N-dimethyl-1H-2-benzopyran-1-propanamine, (syrup).

1-ethyl-N-[2-[bis(4-fluorophenyl)methoxy]ethyl]-3,4-dihydro-6,7,8-trimethoxy-N-methyl-1H-2-benzopyran-1ethanamine, (syrup).

1-ethyl-N-[2-[bis(4-fluorophenyl)butyl]-3,4-dihydro-6,7-dimethoxy-1H-2-benzopyran-1-ethanamine (±)-2,3-dihydroxybutanedioate (1:1) salt, m.p. 75° C.

We claim:

1. An isochromane derivative of the formula

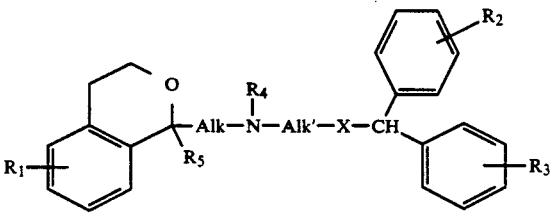

in which each of $R_1$, $R_2$, and $R_3$ is one to four substituents independently selected from hydrogen, hydroxy, alkyl (1–4 C), alkoxy (1–4 C), halogen, or $CF_3$, or represents a methylenedioxy group;

$R_4$ is selected from hydrogen or alkyl (1–4 C);

Alk is an alkylene group with 1–4 carbon atoms; Alk' is an alkylene group with 2–4 carbon atoms, when $R_5$ is selected from hydrogen or alkyl (1–4 C) and X is O or S; or Alk' is an alkylene group with 1–4 carbon atoms or a bond, when $R_5$ is an alkyl (1–4 C) group and X is $CH_2$ or a bond;

or a pharmaceutically acceptable salt thereof.

2. The isochromane derivative of claim 1, in which $R_1$ represents one or two methoxy groups, or a methylenedioxy group, $R_2$ and $R_3$ are hydrogen or halogen, Alk is an unbranched alkylene group with 1–3 carbon atoms, Alk' is 1,2-ethanediyl, and X is O or S, and $R_5$ is selected from hydrogen or alkyl (1–4 C); or a pharmaceutically acceptable salt thereof.

3. The isochromane derivative of claim 1 having the formula

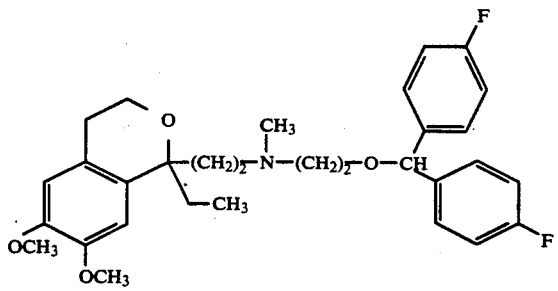

or a pharmaceutically acceptable salt thereof.

4. A pharmaceutical composition comprising an isochromane derivative according to claim 1 and pharmaceutically acceptable auxiliaries.

* * * * *